United States Patent [19]

DeLuca et al.

[11] 4,360,471
[45] Nov. 23, 1982

[54] 23-DEHYDRO-25-HYDROXYVITAMIN $D_3$

[75] Inventors: Hector F. DeLuca; Heinrich K. Schnoes; Joseph K. Wichmann, all of Madison, Wis.

[73] Assignee: Wisconsin Alumni Research Foundation, Madison, Wis.

[21] Appl. No.: 329,845

[22] Filed: Dec. 11, 1981

[51] Int. Cl.³ .............................................. C07J 9/00
[52] U.S. Cl. ................................................. 260/397.2
[58] Field of Search ...................... 260/397.2; 424/236

[56]  References Cited

U.S. PATENT DOCUMENTS 4,263,214  4/1981  DeLuca et al. ................... 260/397.2
4,292,250  9/1981  DeLuca et al. ................... 260/397.2

Primary Examiner—Elbert L. Roberts
Attorney, Agent, or Firm—Howard W. Bremer

[57]  ABSTRACT

A novel vitamin $D_3$ compound, 23-dehydro-25-hydroxyvitamin $D_3$, and hydroxy-protected derivatives thereof are provided. The new compound is a side-chain-desaturated analog of 25-hydroxycholecalciferol, and would find application as a substitute for such compound or for vitamin $D_3$.

4 Claims, No Drawings

23-DEHYDRO-25-HYDROXYVITAMIN $D_3$

This invention relates to a novel vitamin D derivative.

More specifically, this invention relates to a 25-hydroxyvitamin $D_3$ derivative (25-hydroxycholecalciferol) containing a double bond in the side chain, and to acylated or silylated derivatives thereof.

Vitamin $D_3$ is a well-known agent for the maintenance of calcium and phosphorus homeostasis in animals or humans and is widely used therapeutically for the prevention of rickets and other bone diseases. It is now firmly established that the biological efficacy of vitamin D depends on its metabolic conversion, in vivo, to hydroxylated derivatives. A number of such biologically-active hydroxy derivatives are known, including, for example, 25-hydroxyvitamin $D_3$, 1,25-dihydroxyvitamin $D_3$, 24,25-dihydroxyvitamin $D_3$, and 25,26-dihydroxyvitamin $D_3$. The isolation and characterization of these compounds and their biological potency are well-documented in the patent and other literature.

A new hydroxyvitamin D derivative has now been found. This new compound is characterized by hydroxy substitution at carbon 25 and by a double bond between carbons 23 and 24, a feature not previously encountered in heretofore known vitamin D derivatives or metabolites. This compound can be represented by the formula (I) shown below, and can be referred to as 23-dehydro-25-hydroxyvitamin $D_3$ or 23-dehydro-25-hydroxycholecalciferol.

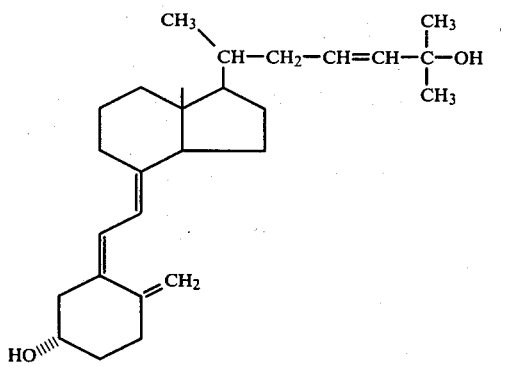

This compound was obtained from the blood of chickens receiving high doses of vitamin $D_3$ according to the following procedure:

Plasma Procurement and Extraction

Sixty twelve-week-old, white Leghorn cockerels (Northern Hatcheries, Beaver Dam, WI) raised on a commercial diet (Ralston Purina, St. Louis, MO) were each dosed intramuscularly with $10^5$ I.U. vitamin $D_3$ (Aldrich Chemicals, Milwaukee, WI) in 50 $\mu$l of ethanol daily for three days. The vitamin purity was found to be >99.9% by high-performance liquid chromatography (HPLC). On the fourth day, each chick was dosed intramuscularly with a total of $1.5 \times 10^7$ I.U. vitamin $D_3$. Four days after this dose, blood was collected by cardiac puncture. The blood was centrifuged to remove cells and the resulting plasma was extracted with 3 volumes of methanol/chloroform (2:1) overnight at approximately 4°–10° C., after which time another volume of chloroform was added, and the organic phase was separated. The aqueous phase was again extracted with half a volume of chloroform, and the combined organic phases were evaporated for subsequent chromatography.

Chromatographic Purification of the Metabolite

The extract from 1160 ml of plasma was chromatographed on a 3×30 cm Sephadex LH-20 column (Pharmacia, Piscataway, NJ) eluted with hexane/methanol/chloroform (9:1:1). Eighty 23 ml fractions were collected. The presence of viatmin D metabolites was detected using the competitive protein binding assay described by Shepard et al. (Biochem J. 182, 55, 1979). The binding peak, eluting in the 25-hydroxyvitamin $D_3$ (25-OH-$D_3$) region was collected. This sample was then chromatographed on a 2×57 cm Lipidex 5000 column (Packard Instrument Co., Downers Grove, IL) eluted with hexane/chloroform (92:8). Sixty 16 ml fractions were collected and assayed as above. The fractions in the 25-OH-$D_3$ region were pooled and the solvent removed by evaporation under vacuum.

The sample was further purified by HPLC using a Waters model ACP/GPC 204 instrument (Waters Associates, Inc., Milford, MA) equipped with a model 450 variable wavelength detector and wavelength drive attachedment and using a 0.45×25 cm microparticulate silica column (Zorbax-SIL, Dupont, Inc., Wilmington, DE) eluted with 2% 2-propanol in hexane. On this system standard 25-OH-$D_3$ elutes at about 36 ml. The material reactive in the binding protein assay and eluting just prior to the 25-OH-$D_3$ standard was pooled for isolation of the 23-dehydro metabolite. This collected material was then chromatographed on HPLC, using a 0.45×25 cm reverse-phase column (octadecylsilane bonded to silica; Zorbax-ODS, Dupont, Inc., Wilmington, DE) eluted with 15% water in methanol. 25-OH-$D_3$ elutes at about 28 ml on this system. The metabolite 23-dehydro-25-hydroxyvitamin $D_3$, exhibiting activity in the binding protein assay, was collected. The compound exhibited a U.V. absorption maximum at $\lambda_{max} = 265$ nm.

Final purification of the compound was performed on HPLC using a 0.45×25 cm microparticulate silica column eluted with 4% of 2-propanol in hexane, and the desired product was collected for structural characterization.

Identification of the Product

The isolated compound exhibited a maximum of 265 nm in the ultraviolet spectrum, indicating the presence of a 5,6-cis-triene chromophore typical of vitamin D. In the mass spectrum major ions and their relative intensities are: m/z 398, 11%, $M^+$; 380, 5%, $M^+$-$H_2O$; 271, 2%, $M^+$ side chain; 253, 5%, 271-$H_2O$; 136, 100% (A-ring+C6+C7)$^+$; 118, 74%, 136-$H_2O$. The prominent peaks at m/z 136 and 118 (136-$H_2O$) which arise from ring A plus carbons 6 and 7 of the vitamin D molecule establish that the vitamin D-ring A moiety is unaltered. Furthermore, the presence of the peaks at m/z 271 and 253 (271-$H_2O$), which arise by loss of the entire side chain, prove that all metabolic alterations have occurred in the side chain. The molecular ion of m/z 398 is consistent with the incorporation of an oxygen atom and an unsaturation in the side chain. Likely side chain modifications consistent with these data include (a) the formation of a carbonyl functionality, (b) the formation of a cyclic ether (e.g. epoxide), and (c) the presence of a hydroxy group plus double bond. To check for the presence of a carbonyl or ether function, the compound was treated with excess NaBH₄ (in methanol solution at room temperature for 30 minutes) and then trimethylsilylated (by treatment of the recovered product with excess N,O-bis-trimethylsilyl-trifluoroacetamide containing 1% trimethylsilyl chloride in pyridine solution). The resulting trimethylsilyl ether (TMS-ether) product shows the following mass spectrum: m/z 542, 22%, M+; 527, 8%, M+-CH₃; 452, 18% M+-HOTMS; 437, 8%, 452-CH₃; 208, 60% (TMS-A-ring+C6+C7)+; 131, 56%, C₃H₆OTMS+; 118, 100%, 208-HOTMS. The molecular ion at m/z 542 indicates formation of a ditrimethylsilyl ether derivative of a diol of molecular weight 398 (i.e. the molecular weight of the original metabolite). This result elimates ketone and cyclic ether structures and indicates an unsaturated monohydroxylated side chain. The C-25-position of the hydroxy group can be deduced from the prominent ion at m/z 131 (which represents the ion (CH₃)₂C=O—Si(CH₃)₃+ and originates from carbons 25,26 and 27 of the side chain), whereas the ions at 208 (A-ring++C6+C7) and 118 are characteristic fragments of vitamin D-3β-OTMS derivatives and reconfirm an intact A-ring moiety.

The presence and the position of the side chain double bond was established by ozonolysis of the compound and gas chromatography-mass spectrometric analysis of the ozonolysis product using methane chemical ionization. Ozonolysis was accomplished by treating a methylene chloride solution of the metabolite at −78° C. with a methylene chloride solution saturated with ozone, and adding after 2 minutes a solution of triphenylphosphine in methylene chloride. The mixture was then warmed to room temperature, and after evaporation of solvent, the ozonolysis product was directly analyzed by combined gas chromatography-mass spectrometry using a Finnigan model 4000 gas chromatograph-mass spectrometer (Finnigan Corp., Sunnyvale, CA) operating in the chemical ionization mode with methane gas, and using a chromatographic column (2 m×2 mm, 3% OV-1) with methane as carrier/reagent gas at 30 ml/minute. The ozonolysis product gave a protonated molecular ion (M+H)+ at m/z 223 and low intensity adduct ions at m/z 251 (M+C₂H₅)+ and 263 (M+C₃H₅)+. This result establishes a molecular weight of 222 for this ozonolysis product as required for the keto-aldehyde of the structure shown below:

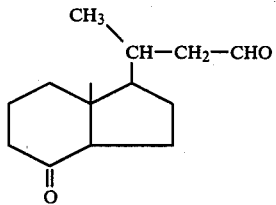

This keto-aldehyde product results from the expected ozonolytic cleavage of a C-7,8 and a C-23,24-double bond and thus proves the presence of a side chain double bond between carbons 23 and 24 of the metabolite.

Therefore, this novel compound is identified as 23-dehydro-25-hydroxyvitamin D₃, as depicted by formula I above.

This compound can be acylated or alkysilylated to yield the corresponding mono- or dihydroxy-protected derivatives by procedures well known in the art. Acyl derivatives that can be readily prepared include, for example, the acetyl, propionyl, butyryl, trifluoroacetyl, trichloroacetyl, benzoyl, nitrobenzyl or halobenzoyl derivatives. These derivatives are prepared by treating the compound with the appropriate acid-anhydride or acylhalide. For example, treatment of the compound with acetic anhydride at room temperature gives the 3-monoacetyl derivatives, whereas treatment at elevated temperatures (50°–100° C.) yields the 3,25-diacetyl products. The diacylated products in turn can be selectively deacylated (e.g. 5% KOH/MeOH) to give the 25-mono-O-acyl derivatives and the C-3 or C-25-monoacyl analogs can then be further acylated at the free hydroxy function with different acyl groups or may be alkylsilyated by well-established procedures, e.g. by treatment with an alkylsilyl chloride reagent in pyridine, where the term "alkyl" donates a hydrocarbon radical of from 1 to about 5 carbons, such as methyl, ethyl, propyl, butyl, tert.-butyl, etc. In this manner, derivatives of 23-dehydro-25-hydroxyvitamin D₃, with different O-acyl or O-alkylsilyl groups at C-3 and C-25, and/or mixed acyl and alkylsilyl groups are readily available.

The novel product of this invention is thus shown to be a side chain desaturated analog of the biologically-potent vitamin D metabolite, 25-hydroxyvitamin D₃. By virtue of such structural relationship, the compound would find application as a substitute for 25-hydroxyvitamin D₃, or as a substitute for vitamin D₃, in various therapeutic or other applications. Moreover, because of the presence of the 23,24-double bond the compound is less likely to undergo, in vivo, the known 24-hydroxylation of 25-hydroxyvitamin D₃ which reduces the bio-potency of the latter compound, and may thus represent a preferred analog for medical applications.

Having thus described the invention, what is claimed is:

1. A compound having the formula

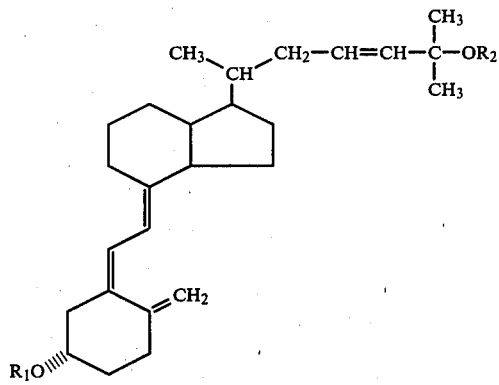

wherein each of R₁ and R₂ is selected from the group consisting of hydrogen, acyl and alkylsilyl.

2. The compound according to claim 1 wherein each of R₁ and R₂ are selected from the group consisting of acetyl, and benzoyl.

3. 23-dehydro-25-hydroxyvitamin D₃.

4. The compound of claim 3 in crystalline form.